United States Patent [19] [11] 4,104,051
Cheng [45] Aug. 1, 1978

[54] SUBSTITUTED BROMO- OR CHLORO-ACETAMIDE HERBICIDES

[75] Inventor: Jiin Duey Cheng, Wilmington, Del.

[73] Assignee: E. I. Du Pont de Nemours and Company, Wilmington, Del.

[21] Appl. No.: 820,883

[22] Filed: Aug. 1, 1977

Related U.S. Application Data

[62] Division of Ser. No. 667,279, Mar. 15, 1976, Pat. No. 4,055,410.

[51] Int. Cl.² ............... A01N 9/22; C07D 233/72
[52] U.S. Cl. ............................................. 71/92; 548/312
[58] Field of Search ............................. 548/312; 71/92

[56] References Cited

U.S. PATENT DOCUMENTS 2,881,171  4/1959  Hankins ............................ 548/320
3,769,301  10/1973 Olin .................................. 71/118
3,907,544  9/1975  Olin .................................. 71/92

OTHER PUBLICATIONS

Svetkin et al., J. of Org. Chem., U.S.S.R., vol. 7, pp. 1339–1340 (1971).

Primary Examiner—Natalie Trousof
Assistant Examiner—N. Harkaway

[57] ABSTRACT

Herbicidal bromo- or chloroacetamides of the formula:

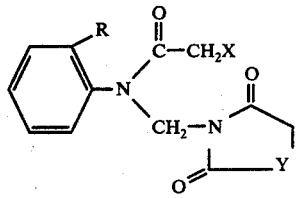

where
R is alkyl or alkoxy of 1 to 4 carbon atoms;
X is chlorine or bromine; and
Y is S or N—CH₃.

12 Claims, No Drawings

SUBSTITUTED BROMO- OR CHLORO-ACETAMIDE HERBICIDES

This is a division, of application Ser. No. 667,279, filed 3/15/76, now U.S. Pat. No. 4,055,410.

BACKGROUND OF THE INVENTION

Recently in U.S. Pat. Nos. 3,769,301 and 3,907,544 herbicidal compounds of the general formula:

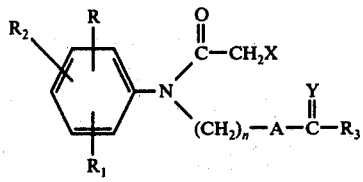

where
X is halogen;
n is 1 or 2;
A is, among others, $-N-(CO)_m-R_4$;
where m is 0, 1, or 2; and
$R_3$ and $R_4$ together can form a alkylene bridge or 2-5 carbons; and
Y is oxygen or sulfur,
were disclosed.

The compounds taught within these patents are active herbicides; the need still exists, however, for herbicides which are more active. The presence of undesired vegetation is very damaging to useful crops such as rice. In the current world situation, wherein food shortages are acute, it is most important not to lose a significant portion of a valuable crop such as rice. The presence of such undesired vegetation results in the loss of a significant portion of such crop. Thus, a need exists for a particularly effective herbicide which will destroy as much of this unwanted vegetation as is possible without causing significant damage to the desired crops, e.g. rice.

According to the instant invention, herbicidal compounds have been discovered which are highly active herbicides and yet cause minimal damage to certain desired crops, e.g. rice.

DESCRIPTION OF THE INVENTION

This invention relates to the novel compounds of Formula I and to agricultural compositions containing them, and to the method of use of these compounds as selective, as well as general, herbicides having both pre- and post-emergence activity:

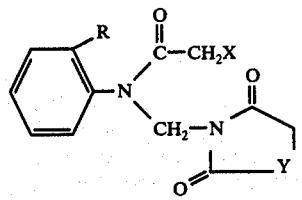

where
R is alkyl or alkoxy of 1 to 4 carbon atoms;
X is chlorine or bromine; and
Y is S or N—$CH_3$.

Preferred, for reasons of economy and/or ease of synthesis and/or higher herbicidal activity, are the compounds of Formula I where, independently:
(I) R is alkyl or alkoxy of 1 or 2 carbon atoms; or
(II) X is chlorine.

More preferred for their outstanding biological activity are those compounds of Formula I wherein R is methyl or methoxy, X is chlorine, and Y is S. Specifically preferred are the compounds:
(a) 2-chloro-N-(2,4-dioxothiazolidin-3-ylmethyl)-N-(2-methylphenyl)acetamide, m.p. 134°–137° C;
(b) 2-chloro-N-(2,4-dioxothiazolidin-3-ylmethyl)-N-(2-methoxyphenyl)acetamide, m.p. 188°–191° C.

DETAILED DESCRIPTION OF THE INVENTION

The novel compounds of this invention are prepared by haloacetylation of the corresponding anilines (II) in an aprotic solvent such as toluene, chloroform, benzene, and the like in the presence of an acid acceptor such as triethylamine, pyridine, etc., as shown by Equation A.

The reaction takes place at a temperature of about −30° to 80° C, preferably −10° to 5° C over a period of about 30 minutes to 5 hrs, preferably about 1 to 3 hrs.

Equation A

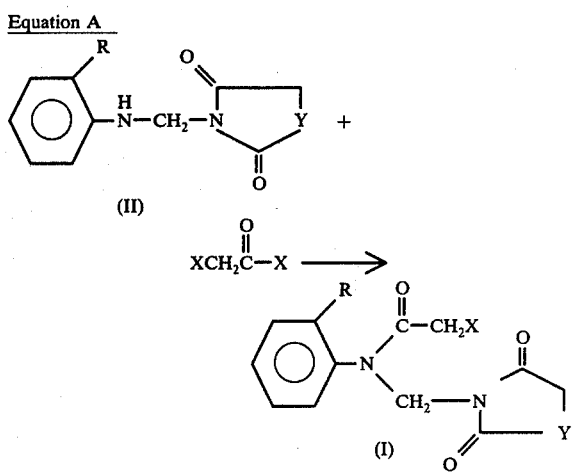

The anilines (II) are prepared by the condensation of 2-substituted aniline, formaldehyde and the corresponding imide under the conditions of Mannich reaction [Kadin, J. Org. Chem. 38, 1348 (1973); Kononenko, et al., J. Org. Chem. USSR, 9, 59 (1973)], which is herein incorporated by reference, as given by Equation B.

Equation B

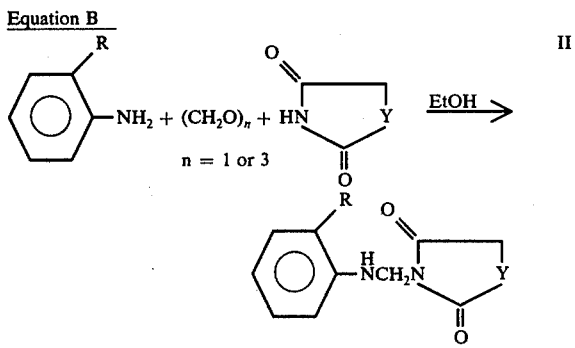

The preparation of the novel compounds of the present invention is illustrated by the following examples.

EXAMPLE 1

2-Chloro-N-(2,4-dioxothiazolidin-3-ylmethyl)-N-(2-methylphenyl)acetamide

A mixture of 10.7 g of o-toluidine, 3.3 g. of paraformaldehyde, and 11.7 g of 2,4-thiazolidinedione in 100 ml of absolute ethanol was refluxed 5 hrs under nitrogen atmosphere. On cooling, the resulting precipitate was filtered off to give 22.1 g of N-(2-methylphenylaminomethyl)-2,4-thiazolidinedione, mp 109°–111° C; identified by IR and NMR.

A solution of 4.5 g of chloroacetyl chloride in 10 ml of toluene was added dropwise to a suspension of 7.8 g of N-(2-methylphenylaminomethyl)-2,4-thiazolidinedione and 3 g of pyridine in 80 ml of toluene at −5° C with stirring and kept on an ice bath for 3 hrs. The resulting precipitate was filtered and washed with water to give 2-chloro-N-(2,4-dioxothiazolidin-3-ylmethyl)-N-(2-methylphenyl)acetamide, mp 133°–136° C. The toluene filtrate was extracted with two 50 ml portions of 5% hydrochloric acid, 50 ml of water, dried over anhydrous magnesium sulfate and filtered. The filtrate was evaporated on a rotary evaporator to give the product which was crystallized from benzene-ether, mp 134°–137° C. The total yield was 6.0 g [$M^+$ = 312 (molecular ion by mass spec.)].

EXAMPLE 2

2-Chloro-N-(2,4-dioxothiazolidin-3-ylmethyl)-N-(2-methoxyphenyl)acetamide

A mixture of 13.3 g of 2,4-thiazolidinedione and 12.3 g of o-anisidine was dissolved in 100 ml of warm ethanol at 55° to 70° C. The solution was cooled to about 30° C, and 9.1 ml of 37% formaldehyde solution was added and stirred overnight. The resulting precipitate was filtered to give 22.5 g of N-(2-methoxyphenylaminomethyl)-2,4-thiazolidinedione, mp 88.5°–91° C; identified by IR and NMR.

A suspension of 7 g of anhydrous potassium carbonate, 7.3 g of N-(2-methoxyphenylaminomethyl)-2,4-thiazolidinedione, and 5.3 g of chloroacetyl chloride in 50 ml of chloroform was cooled in an ice bath and stirred at ambient temperature for 48 hrs. The resulting precipitate was filtered, washed with water and recrystallized from nitromethane-ethanol to give 5.6 g of 2-chloro-N-(2,4-dioxothiazolidin-3-ylmethyl)-N-(2-methoxyphenyl)acetamide; mp 188°–191° C; $M^+$ = 328.

Cal'd for $C_{13}H_{13}ClN_2O_4S$: C: 47.49; H: 3.99; Cl: 10.78; N: 8.52; S: 9.75. Found: C: 47.8; H: 4.16; Cl: 11.55; N: 8.59; S: 9.73.

EXAMPLE 3

2-Chloro-N-(2,4-dioxo-1-methylimidazolidin-3-ylmethyl)-N-(2-methoxyphenyl)acetamide A mixture of 12.3 g of o-anisidine, 3.3 g of paraformaldehyde, and 11.4 g of 1-methylhydantoin in 100 ml of absolute ethanol was refluxed for 8 hrs under nitrogen atmosphere. At the end of this time, the solution was cooled on a dry ice-acetone bath and the solvent was decanted to leave a viscous oil. The oil was dissolved in 800 ml of ether and the ethereal solution was allowed to evaporate slowly at room temperature. The resulting precipitate was filtered to give 12 g of 1-methyl-3-(2-methoxyphenylaminomethyl)hydantoin, mp 93°–96.5° C, identified by IR and NMR.

A solution of 4.5 g of chloroacetyl chloride in 10 ml of toluene was added dropwise to a solution of 7 g of the 1-methyl-3-(2-methoxyphenylaminomethyl)hydantoin and 2.8 g of pyridine in 40 ml of toluene at −10° C. The suspension was stirred on an ice-bath for 1.5 hrs. The resulting precipitate was filtered and thoroughly washed with 5% hydrochloric acid, water, and recrystallized from chloroform-ether to give 6.0 g of N-(2,4-dioxo-1-methylimidazolidin-3-ylmethyl)-N-(2-methoxyphenyl)acetamide, mp 169°–172° C; $M^+$ = 325.

The following compounds were also prepared by the general method set forth in the preceding examples.

| Compounds | Physical Property |
| --- | --- |
| 2-Chloro-N-(2,4-dioxothiazolidin-3-ylmethyl)-N-(2-ethoxyphenyl)-acetamide | mp 124.5–125.5° C |
| 2-Chloro-N-(2,4-dioxothiazolidin-3-ylmethyl)-N-(2-ethylphenyl)-acetamide | mp 151.5–152.5° C |
| 2-Chloro-N-(2,4-dioxothiazolidin-3-ylmethyl)-N-(2-isopropylphenyl)-acetamide | mp 141–143° C |
| 2-Chloro-N-(2,4-dioxothiazolidin-3-ylmethyl)-N-(2-isopropoxyphenyl)-acetamide | oil |
| 2-Chloro-N-(2,4-dioxothiazolidin-3-ylmethyl)N-(2-sec-butylphenyl)-acetamide | mp 120–123° C |
| 2-Chloro-N-(2,4-dioxo-1-methyl-imidazolidin-3-ylmethyl)-N-(2-ethoxyphenyl)acetamide | mp 126–127° C |
| 2-Chloro-N-(2,4-dioxo-1-methyl-imidazolidin-3-ylmethyl)-N-(2-ethylphenyl)acetamide | mp 92–95° C |
| 2-Chloro-N-(2,4-dioxo-1-methyl-imidazolidin-3-ylmethyl)-N-(2-isopropylphenyl)acetamide | oil |
| 2-Chloro-N-(2,4-dioxo-1-methyl-imidazolidin-3-ylmethyl)-N-(2-methylphenyl)acetamide | mp 84–92° C |
| 2-Chloro-N-(2,4-dioxo-1-methyl-imidazolidin-3-ylmethyl)-N-(2-sec-butylphenyl)acetamide | oil |
| 2-Chloro-N-(2,4-dioxo-1-methyl-imidazolidin-3-ylmethyl)-N-(2-isopropoxyphenyl)acetamide | oil |

Other compounds of this invention include the following:

2-Chloro-N-(2,4-dioxothiazolidin-3-ylmethyl)-N-(2-n-propoxyphenyl)acetamide;

2-Chloro-N-(2,4-dioxothiazolidin-3-ylmethyl)-N-(2-n-butylphenyl)acetamide;

2-Chloro-N-(2,4-dioxothiazolidin-3-ylmethyl)-N-(2-n-butoxyphenyl)acetamide;

2-Bromo-N-(2,4-dioxothiazolidin-3-ylmethyl)-N-(2-methoxyphenyl)acetamide;

2-Bromo-N-(2,4-dioxothiazolidin-3-ylmethyl)-N-(2-methylphenyl)acetamide;

2-Bromo-N-(2,4-dioxo-1-methylimidazolidin-3-ylmethyl)-N-(2-n-propoxyphenyl)acetamide;

2-Chloro-N-(2,4-dioxo-1-methylimidazolidin-3-ylmethyl)-N-(2-n-butylphenyl)acetamide;

2-Chloro-N-(2,4-dioxo-1-methylimidazolidin-3-ylmethyl)-N-(2-n-butoxyphenyl)acetamide;

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", McCutcheon's Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer- or fluid-energy-mill. Suspensions are prepared by wet-milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th. Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 4

| Wettable Powder | |
| --- | --- |
| 2-chloro-N-(2,4-dioxothiazolidin-3-yl-methyl)-N-(2-methylphenyl)acetamide | 50% |
| sodium alkylnaphthalenesulfonate | 2% |
| low viscosity methyl cellulose | 2% |
| diatomaceous earth | 46% |

The ingredients are blended, coarsely hammer-milled and the air milled to produce particles of active essentially all below 10 microns in diameter. The product is reblended before packaging.

EXAMPLE 5

| Wettable Powder | |
| --- | --- |
| 2-chloro-N-(2,4-dioxothiazolidin-3-ylmethyl)-N-(2-methoxyphenyl)acetamide | 80% |
| sodium alkylnaphthalenesulfonate | 2% |
| sodium ligninsulfonate | 2% |
| synthetic amorphous silica | 3% |
| kaolinite | 13% |

These components are blended, micropulverized until the particles are essentially under 50 microns in size, and then reblended.

EXAMPLE 6

| Granule | |
| --- | --- |
| wettable powder of Example 5 | 15% |
| gypsum | 69% |
| potassium sulfate | 16% |

The ingredients are blended in a rotating mixer and water is sprayed on to accomplish granulation. When most of the material has reached the desired range of 1.0 to 0.42 mm (U.S.S. #18 to 40 sieves), the granules are removed, dried, and screened. Oversize material is crushed to produce additional material in the desired range. These granules contain 12% active ingredient.

EXAMPLE 7

| Solution | |
| --- | --- |
| 2-chloro-N-(2,4-dioxothiazolidin-3-yl-methyl)-N-(2-methylphenyl)acetamide | 30% |
| dimethylformamide | 70% |

The ingredients are combined and stirred to produce a solution, which can be used for low volume applications.

EXAMPLE 8

| Aqueous Suspension | |
| --- | --- |
| 2-chloro-N-(2,4-dioxothiazolidin-3-yl-methyl)-N-methoxyphenyl)acetamide | 25% |
| hydrated attapulgite | 3% |
| crude calcium ligninsulfonate | 10% |
| Sodium dihydrogen phosphate | 0.5% |
| water | 61.5% |

The ingredients are ground together in a ball- or roller-mill until the solid particles have been reduced to diameters under 10 microns.

Utility

The compounds of Formula I are useful for the control of undesired vegetation in crops. More particularly, the compounds of the present invention control barnyardgrass (*Echinochloa spp.*) in rice cultures.

The compounds of the present invention are most effective against barnyardgrass when applied prior to emergence of barnyardgrass plants from the soil. They may be applied in upland (dry) cultures or in paddy (flooded) cultures.

The precise amount of the compounds of the present invention to be used will vary according to the cultural method employed, the soil type, weather, etc. However, broadly speaking, they are used at rates of about 0.12 kg to about 12 kg, preferably 0.25 to 6 kg, per hectare. The lower rates in this range will generally be selected on sandy soils low in organic matter content or in situations where maximum persistence is not necessary.

The compounds of the present invention may be applied singly or in admixture with other herbicides, including but not restricted to: 1-(p-cumyl)-3,3-dimethylurea; 2,4,6-trichlorophenyl-4′-nitrophenylether; 2-methylthio-4,6-bis(ethylamino)-s-triazine; ethyl hexahydrothiol-1-azepinecarboxylate.

The effectiveness of the compounds of Formula I against barnyardgrass in rice is illustrated by the following tests.

Procedure, Test 1

Seeds of crabgrass (*Digitaria sp.*), barnyardgrass (*Echinochloa crusgalli*), wild oats (*Avena fatua*). *Cassia tora*, morningglory (*Ipomoea spp.*), cocklebur (*Xanthium sp.*), sorghum, corn, soybean, rice, wheat and nutsedge tubers were planted in a growth medium and treated preemergence with the chemicals dissolved in a nonphytotoxic solvent. At the same time, cotton having five leaves (including cotyledonary ones), bush beans with the second trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three-five leaves were sprayed. Treated plants and controls were maintained in a greenhouse for sixteen days, then all species were compared to controls and visually rated for response to treatment.

Ratings for compounds tested by this procedure are recorded in Table 1.

TABLE 1

PLANT RESPONSE TEST 1

POST EMERGENCE

| Compound | Kg/Ha | Bushbean | Cotton | Morning Glory | Cocklebur | Cassia | Nutsedge | Crabgrass | Barnyard Grass | Wild oats | Wheat | Corn | Soybean | Rice | Sorghum |
|---|---|---|---|---|---|---|---|---|---|---|---|---|---|---|---|
| [structure with CH₃O-phenyl] | 2 | 0 | 0 | 2G | 0 | 0 | 2G | 6H | 2C 9H | 0 | 0 | 0 | 0 | 3G | 0 |
| [structure with CH₃-phenyl] | 2 | 0 | 0 | 0 | 0 | 0 | 0 | 2H | 9H | 0 | 0 | 0 | 0 | 0 | 0 |

PRE-EMERGENCE

| Compound | Kg/Ha | Morning Glory | Cocklebur | Cassia | Nutsedge | Crabgrass | Barnyard Grass | Wild oats | Wheat | Corn | Soybean | Rice | Sorghum |
|---|---|---|---|---|---|---|---|---|---|---|---|---|---|
| [structure with CH₃O-phenyl] | 2 | 0 | 2H | 0 | 0 | 10E | 10H | 2G | 0 | 0 | 9H | 5E | 0 |

TABLE 1-continued

PLANT RESPONSE TEST 1

| Compound | | | | | | | | | | | | | |
|---|---|---|---|---|---|---|---|---|---|---|---|---|---|
| [structure: thiazolidinedione with N-CH₂-N(CCH₂Cl)(o-tolyl)] | 2 | 0 | 0 | 2G | 0 | 7H | 10H | 0 | 0 | 0 | 0 | 0 | 0 |

The plant response ratings above are composed of a number and a letter. The number describes the extent of the response and ranges from zero to ten with zero representing no response, and ten representing 100% response. The letter describes the type of the response, with "C" representing chlorosis-necrosis, "E" representing emergence inhibited, "G" growth retarded, and approximately 5 mm of water over a period of 180 minutes. From this point the plantings were maintained in the greenhouse and watered on a demand basis. Plant response ratings were made around 4 weeks after planting and treatment.

The same rating procedure and symbols as mentioned in Test 1 apply for Test 2.

PLANT RESPONSE TEST 2

| Compound | Rate Kg/Ha | Rice | Barn-yard-grass | Wheat | Wild Oats | Crab-grass | Sor-ghum | John-son-grass | Giant Fox-tail | Blue-grass | Cheat-grass | Corn |
|---|---|---|---|---|---|---|---|---|---|---|---|---|
| [structure with CH₃O] | ¼ | 4H | 8H | 0 | 0 | 9H | 0 | 0 | 7H | 0 | 2C | 0 |
| | 0 | 0 | 3G | 0 | 0 | 3G | 0 | 0 | 4G | 0 | 0 | 0 |

| Compound | Rate Kg/Ha | Mus-tard | Coc-kle-bur | Pig-weed | Nut-sedge | Curly indigo | Morn-ing-glory | Cassia | Tea-weed | Vel-vet-leaf | Jim-son-weed | Soy-bean | Sugar beet |
|---|---|---|---|---|---|---|---|---|---|---|---|---|---|
| [structure with CH₃O] | ¼ | 0 | 0 | 0 | 0 | 0 | 0 | 0 | 0 | 0 | 0 | 0 | 0 |
| | | 0 | 0 | | 0 | 0 | 0 | 0 | 0 | 0 | 0 | 0 | 0 |

"H" formative effect (malformation or hormone type).

Additional greenhouse tests have been conducted, as described below:

Procedure, Test 2

A medium-textured soil, fairly low in organic matter content, was planted to seeds of the species listed in the following table. Planting depth was about 0.5 cm except for corn and soybeans which were planted at a depth of 2.5 cm. The test compounds were dissolved/suspended in a nonphytotoxic solvent. Within a few hours of planting, the test solutions were applied to the soil surface. The rates of application for the test compounds are shown in the table. Immediately after treatment the soil surfaces were exposed to simulated rainfall at the rate of Procedure, Test 3

A medium-textured soil, fairly low in organic matter content, was planted with the species listed in the table below. The plantings were maintained in a moist condition for 2 to 3 weeks until most species were in the 2- to 4-leaf stage of development. The test compounds were dissolved/suspended in a non-phytotoxic solvent which was applied as overall solid/foliage treatments to the mixed stand of young crops and weeds at the rates given in the attached table. The plantings were then maintained in the greenhouse where they were watered on a demand basis. Plant response ratings were made around 2 weeks after treatment.

PLANT RESPONSE TEST 3

| Compound | Kg/ha | Soy-bean | Corn | Cot-ton | Rice | Wheat | Vel-vet-leaf | Ses-ban-ia | Cas-sia |
|---|---|---|---|---|---|---|---|---|---|

-continued
PLANT RESPONSE TEST 3

| Compound | Kg/ha | Morning-glory | Alf-alfa | Jim-son-weed | Coc-kle-bur | Crab-grass | Barn-yard grass | Giant Fox-tail | Wild-Oats | Sor-ghum | Nut-sedge |
|---|---|---|---|---|---|---|---|---|---|---|---|
| [structure: thiazolidinedione with N-CH₂N(CH₂-tolyl)-C(O)CH₂Cl] | ½ ¼ | 4B 2B | 2B 0 | 7B 3B | 0 0 | 0 0 | 9B 2C | 6B 2B | | 3B 2B | |
| [structure: thiazolidinedione with N-CH₂N(CH₂-tolyl)-C(O)CH₂Cl] | ½ ¼ | 2B 0 | 3B 2C | 8B 2C | 2B 1B | 0 0 | 2B 0 | 2C 2C | 0 0 | 3B 0 | 0 0 |

The same rating procedure and symbols as mentioned in Test 1 apply for Test 3.

Procedure, Test 4

The test compound was applied in an overall spray in a nonphytotoxic solvent containing a wetting agent and a humectant to pots (pre-emergence) containing seeds of an intermediate (hydrid) rice, a japonica rice, barnyardgrass (*Echinochloa sp.*), curly indigo (*Aeschynomene virginica*), and wild morningglory *Convolvulus arvensis*), and was also applied to established (post-emergence) plantings of the same species. The treatments were maintained in a greenhouse for three weeks after which plant response ratings were taken. The same rating procedure and symbols as mentioned in Test 1 apply in the present test.

TEST 4

| COMPOUND | RATE Kg/Ha | PRE-EMERGENCE | | | | | POST EMERGENCE | | | | |
|---|---|---|---|---|---|---|---|---|---|---|---|
| | | INTER-MEDIATE RICE | JAPONICA RICE | BARNYARD-GRASS | CURLY INDIGO | WILD MORNING GLORY | INTER-MEDIATE RICE | JAPONICA RICE | BARNYARD-GRASS | CURLY INDIGO | WILD MORNING GLORY |
| ![structure 1] | 4 2 1 ½ | 0 0 0 0 | 0 0 0 0 | 0 4G 10E 9E | 0 0 0 0 | 0 0 0 0 | 0 0 0 1 | 0 0 0 0 | 0 0 0 0 | 0 0 0 1 | 0 0 0 0 |
| ![structure 2] | 4 2 1 ½ | 0 0 0 0 | 0 0 0 0 | 2G 9G 9G 10E | 0 0 0 | 0 0 0 | 1 0 0 0 | 0 0 0 0 | 0 0 0 0 | 0 0 0 0 | 0 0 0 0 |

Procedure, Test 5

The test compound was applied to the water surface of a soil-containing tub (with seeds of barnyardgrass (*Echinochloa sp.*) mixed into the soil) designed to simulate a rice paddy. Two days later rice plants in the three leaf stage were transplanted into the tub. Final plant response ratings, presented below, were taken 21 days after transplanting:

| Compound | Rate, kg/Ha | Plant Response Ratings | |
|---|---|---|---|
| | | Rice | Barnyardgrass |
| (structure with CH₃O) | 0.5 | 1G | 9G |
| (structure with CH₃) | 0.5 | 0 | 9C |

The same rating procedure and symbols as mentioned in Test 1 apply for Test 5.

It should be noted from the tests above that these compounds controlled barnyardgrass and other weeds with little effect on the crop (rice). The preemergence control was especially good.

What is claimed is:

1. A compound of the formula:

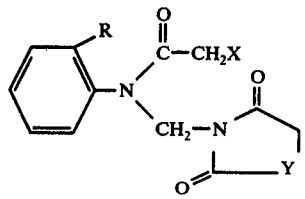

where
R is alkyl or alkoxy of 1 to 4 carbon atoms;
X is chlorine or bromine; and
Y is N—CH₃.

2. A compound of claim 1 wherein R is alkyl or alkoxy of 1 to 2 carbon atoms.

3. A compound of claim 1 wherein X is chlorine.

4. A compound of claim 1 wherein R is methyl or methoxy, and X is chlorine.

5. A composition for the control of undesirable vegetation consisting essentially of a herbicidally effective amount of a compound of claim 1 and at least one of (a) a surface-active agent or (b) a solid or liquid diluent.

6. A composition for the control of undesirable vegetation consisting essentially of a herbicidally effective amount of a compound of claim 2 and at least one of (a) a surface-active agent or (b) a solid or liquid diluent.

7. A composition for the control of undesirable vegetation consisting essentially of a herbicidally effective amount of a compound of claim 3 and at least one of (a) a surface-active agent or (b) a solid or liquid diluent.

8. A composition for the control of undesirable vegetation consisting essentially of a herbicidally effective amount of a compound of claim 4 and at least one of (a) a surface-active agent or (b) a solid or liquid diluent.

9. A method for the control of undesirable vegetation comprising applying to the locus of such undesirable vegetation a herbicidally effective amount of a compound of claim 1.

10. A method for the control of undesirable vegetation comprising applying to the locus of such undesirable vegetation a herbicidally effective amount of a compound of claim 2.

11. A method for the control of undesirable vegetation comprising applying to the locus of such undesirable vegetation a herbicidally effective amount of a compound of claim 3.

12. A method for the control of undesirable vegetation comprising applying to the locus of such undesirable vegetation a herbicidally effective amount of a compound of claim 4.

* * * * *